United States Patent [19]

Arakawa et al.

[11] Patent Number: 5,649,921

[45] Date of Patent: Jul. 22, 1997

[54] PAPER DIAPER RELEASE PART STRUCTURE HAVING AN INTERFACIAL BOUNDARY CONSTITUTED BY A PRESSURE-SENSITIVE ADHESIVE LAYER AND A SILICONE-BASED RELEASE LAYER, A DIAPER CONTAINING A SPECIFIC RELEASE PART STRUCTURE, AND A METHOD FOR REDUCING PEELING NOISE

[75] Inventors: Masaaki Arakawa; Katsumi Hori, both of Osaka, Japan

[73] Assignee: Nitto Denko Corporation, Osaka, Japan

[21] Appl. No.: 225,082

[22] Filed: Apr. 8, 1994

Related U.S. Application Data

[63] Continuation of Ser. No. 856,908, May 12, 1992, abandoned.

[30] Foreign Application Priority Data

| Oct. 16, 1990 | [JP] | Japan | 2-278025 |
| Sep. 30, 1991 | [JP] | Japan | 3-280775 |
| Oct. 16, 1991 | [WO] | WIPO | PCT/JP91/01413 |

[51] Int. Cl.⁶ .................................................. A61F 13/60
[52] U.S. Cl. ........................... 604/390; 428/352; 602/57
[58] Field of Search ........................... 604/390, 389; 602/52, 78, 903, 57; 428/352, 356; 24/304, DIG. 11

[56] References Cited

U.S. PATENT DOCUMENTS

| 3,527,659 | 9/1970 | Keil . |
| 4,123,604 | 10/1978 | Sandford, Jr. . |
| 4,202,925 | 5/1980 | Dabroski ................ 602/903 X |
| 4,393,080 | 7/1983 | Pawelchak et al. ........... 602/52 X |
| 4,778,701 | 10/1988 | Pape et al. .............. 604/390 X |
| 4,808,474 | 2/1989 | Sipinen ................. 604/389 X |
| 5,080,973 | 1/1992 | Nguyen ................... 428/352 |

FOREIGN PATENT DOCUMENTS

| 0108208 | 5/1984 | European Pat. Off. . |
| 0306232 | 3/1989 | European Pat. Off. . |
| 0458581 | 11/1991 | European Pat. Off. . |

OTHER PUBLICATIONS

Chemical Patents Index, Basic Abstracts Journal, Week 8821, 20 Jul. 1988, Derwent Publications Ltd., London, GB; AN 88-144446 for JP-A-63-86786.

*Primary Examiner*—David H. Willse
*Attorney, Agent, or Firm*—Sughrue, Mion, Zinn, Macpeak & Seas

[57] ABSTRACT

A freely peelable release part structure is disclosed. The tape or a like part associated with the structure is difficult to separate when it should be kept fixed. On the other hand, noise-free peeling thereof is easy when it should be peeled away. In particular, a release part structure useful for the fastening of diapers is provided. It contains a structure of a release part whose interfacial boundary is constituted by a pressure-sensitive adhesive layer (4) and a silicone-based release layer (2), characterized in that the adhesive layer comprises a tacky substance containing a rubber as a major component and the release layer comprises a silicone-based release agent containing a three-dimensional structure organopolysiloxane in an amount of 1–80% by weight.

4 Claims, 1 Drawing Sheet

PAPER DIAPER RELEASE PART STRUCTURE HAVING AN INTERFACIAL BOUNDARY CONSTITUTED BY A PRESSURE-SENSITIVE ADHESIVE LAYER AND A SILICONE-BASED RELEASE LAYER, A DIAPER CONTAINING A SPECIFIC RELEASE PART STRUCTURE, AND A METHOD FOR REDUCING PEELING NOISE

This is a continuation of application Ser. No. 07/856,908 filed May 12, 1992, now abandoned.

TECHNICAL FIELD

The present invention relates to a structure of a release part making a reduced peeling noise. Its object is to provide a release part which is utilized as the release part of an adhesive tape mainly for paper diaper use in which a fastener tape is bonded and fixed to a reinforcing film and to the back of a release tape in a freely peelable manner. Further, it is also advantageously used as a release part structure utilized in other disposable absorbent articles such as sanitary napkins and as a release part structure in medical tapes, packaging tapes, and the like.

BACKGROUND ART

In general, the structure of a diaper release part, in which a tape for diaper use such as a fastener tape is fixed, is required to be difficult to cause separation of the fastener tape when the tape should be kept fixed, in order to prevent leakage or slippage during wearing of the diaper. On the other hand, the fastener tape must be easy to peel from the diaper in order for the diaper to be put on and off easily.

For this reason, in the fastener parts of diapers, adhesives which can easily obtain firm bonding have conventionally been used for the fastener tapes. Also, and the diaper front parts have been provided with a reinforcing film for easy peeling, with the surface of this reinforcing film being coated with a long-chain alkyl type release agent having good holding properties which prevent the fastener tape from separating when the tape should be kept fixed.

Although this long-chain alkyl type release agent has exhibited its advantages as an excellent release agent for meeting the above-described demand, there has been a drawback that when mother tries to peel the fastener tape from the reinforcing film, the tape makes a loud noise of "Bari—Bari".

Such a peeling noise has posed a problem, for example, that it awakes the baby in sleep or awakes sleeping persons around the baby. Thus, and an improvement in this respect has been desired.

On the other hand, if silicone-based release agents generally employed for various purposes are used as the release agents for use in adhesive tapes or the like, the tapes or the like do not make such a noise when peeled.

However, since use of the silicone-based release agent greatly reduces the shear bond strength to the adhesive layers of the tapes, application thereof to a diaper fastener part or the like is defective in that the tape is prone to separate off. Hence, the silicone-based release agent is not frequently used in such fixing applications at present.

DISCLOSURE OF THE INVENTION

In view of the above-described problems, the present inventors have studied to utilize the noiseless peel properties of silicone-based release agents. As a result, it has been found that the object can be accomplished in a release part structure constituted by a combination of a specific pressure-sensitive adhesive layer and a specific silicone-based release layer, and the present invention has thus been completed.

That is, the present invention is a structure of a release part whose interfacial boundary is constituted by a pressure-sensitive adhesive layer and a silicone-based release layer, characterized in that the release layer comprises a silicone-based release agent containing an organopolysiloxane having a three-dimensional structure in an amount of 1–80% by weight and the adhesive layer comprises a tacky substance containing a rubber as a major component. This release part structure eliminates the above-described problems.

The present invention will be explained below mainly with respect to its application to the release part structure of a diaper. However, the present invention not only is usable as the release part structures of other disposable absorbent articles such as sanitary napkins, but also is suitable for use as the structure of a release part employing a medical tape because it can be used in hospitals at midnight without disturbing other patients in sleep. Further, it is also useful as release part structures in corrugated boards and the like which employ packaging tapes and are used in large quantities, because their peeling noises are diminished.

Furthermore, in tapes in a rolled state, in which release parts are generally constituted between rolled-tape layers, the release part structure of the present invention is effective in improving workroom environments where peeling noises are involved, because the peeling noises produced when the tapes are unwound are diminished by the application of the release part structure.

It is said that a silicone-based release agent inherently exhibits release properties due to the fact that methyl groups which are the side chains of the dimethylpolysiloxane helical structure face outward from the helix. However, the arrangement of these methyl groups is disordered by mixing an organopolysiloxane having a three-dimensional structure and, as a result, the inherent release properties are lost.

Based on this idea, the present invention has succeeded to obtain shear properties necessary for fixing diaper tapes and the like by using a silicone-based release agent containing 1–80% by weight of an organopolysiloxane having a three-dimensional structure and by using, as the pressure-sensitive adhesive for bonding, a tacky substance containing a rubber as a major component.

The reason why a tacky substance containing a rubber as a major component is employed in the present invention as the pressure-sensitive adhesive layer constituting the release part is that it is thought that high self-holding properties which withstand shear load are obtained due to the high cohesiveness of the rubber constituting the tacky substance and the tacky substance shows good shear properties to the silicone-based release agent described later.

As a result of experiments conducted repeatedly by the present inventors, shear bond strengths not less than 1 kg/25 mm width were obtained in the case of using tacky substances containing a rubber as a major component, whereas only shear bond strengths as low as below 200 g/25 mm width were obtained in the case of using conventional acrylic pressure-sensitive adhesives.

As the tacky substance containing a rubber as a major component, a substance mainly comprising either natural rubber or a synthetic rubber can be used. In particular, however, substances mainly comprising an ABA-type or AB-type block copolymer (wherein A is a thermoplastic block and B is a rubber block; e.g., styrene-isoprene-styrene copolymers, styrene-butadiene-styrene copolymers, styrene-ethylene-butadiene-styrene copolymers, styrene-butadiene copolymers, hydrogenation products thereof, and the like) are preferred from the standpoint of, for example, avoiding environmental pollution by the use of hot-melt coating.

The above-described tacky substance containing a rubber as a major component is applied on a substrate such as a tape support, thereby constituting the pressure-sensitive adhesive layer in the present invention.

The silicone-based release layer constituting the release part in the present invention can be formed of an ordinarily employed silicone-based release agent mainly comprising dimethylpolysiloxane, and either of the addition reaction type and the condensation reaction type can be used.

As the organopolysiloxane having a three-dimensional structure contained in the silicone-based release agent described above, an organopolysiloxane having an average composition formula shown by

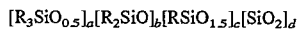

(wherein R is a monovalent hydrocarbon group, and a, b, c, and d, which represent the molar fractions of the respective siloxane units, are as follows; a is 0.1 to 0.6, b is 0 to 0.45, c is 0 to 0.3, and d is 0.3 to 0.8, provided that a/d is 0.3 to 2.0) is suitably used.

The organopolysiloxane having a three-dimensional structure is added in an amount in the range of 1–80% by weight, preferably 5–60% by weight. Its amount below 1% by weight is not preferred in that the effect of imparting the necessary heavypeel strength cannot be obtained, while its amount exceeding 80% by weight is not preferred because the peel strength becomes so heavy that peeling becomes difficult.

It is preferred that the silicone-based release agent containing the organopolysiloxane having a three-dimensional structure in the specified amount be coated by means of solventless coating. However, if the viscosity thereof is too high, it is possible to add a small amount of an organic solvent to lower the viscosity, coat the diluted release agent on a film or tape, and then conduct drying treatment, followed by ultraviolet irradiation treatment or the like.

Incidentally, the silicone-based release agent is coated in an amount of 0.01–10 g/m², preferably 0.1–3 g/m².

Besides coating on the back of each release tape and the back of the reinforcing film in a paper diaper, the above-described silicone-based release agent can be used by directly coating on the surface of the back sheet of a paper diaper.

As the film or tape used as a substrate, those comprising the polypropylene-containing plastic described in Unexamined Published Japanese Patent Application 63-112704, a laminate of a polypropylene and a polypropylene-containing plastic, or a polyester are preferred, and the surface thereof can be either flat or matte.

It is also preferred that a film containing an olefin-based, styrene-based, urethane-based, or polyester-based elastomer as a major component be used as the substrate, because such a substrate shows good slip properties and is soft.

It is preferred that the above-described film or tape be subjected beforehand to a surface treatment such as corona treatment in order to prevent peeling of a release agent to be applied on its surface, and a surface tension of at least 38 dyne/cm² or more is preferred as a measure of the treatment strength.

Application examples utilizing the release part structure of the present invention are explained by reference to the accompanying drawings.

FIG. 1 is an illustrative view showing each part in a paper diaper A, in which B is a back sheet, C is a top sheet in a belt part, D is a reinforcing film, E is a release tape, and F is a fastener tape.

FIG. 2 shows a structure example in which the release part structure of the present invention is used to bond a reinforcing film D on a back sheet B in a paper diaper A with a fastener tape F. On the back sheet B, a film 1 on a surface of which a silicone-based release layer 2 as described above has been formed by coating is bonded by means of an adhesive 3. On the other hand, on the release layer 2 of this reinforcing film D, the fastener tape F prepared by forming on a tape support 5 a pressure-sensitive adhesive layer 4 comprising a tacky substance containing a rubber as a major component is bonded and fixed through the layer 4 in a freely peelable manner, with a release part of the present invention being constituted at the interfacial boundary between the layer 2 and the layer 4.

Additionally, in place of the above construction, the release part may have a construction formed by directly heat-bonding a film 1 having a release layer 2 on its surface onto the back sheet B, or a construction formed by directly coating the release agent used in the present invention on the back sheet B of the paper diaper A.

FIG. 3 shows an example in which the fixing structure of the present invention is applied to a sanitary napkin. One end part of the napkin N is provided on its inner side with a pressure-sensitive adhesive layer 4 consisting of a tacky substance containing a rubber as a major component, while the other end part is provided on its inner side with a release layer 2 comprising the above-described silicone-based release agent. The napkin N is folded such that the pressure-sensitive adhesive layer 4 contacts with the upper side of the release layer 2, with a release part of the present invention being constituted at the interfacial boundary between the layer 2 and the layer 4.

FIG. 4 shows an example in which the fixing structure of the present invention is applied to a rolled tape T. Illustratively stated, the tape T is provided on its inner side with a pressure-sensitive adhesive layer comprising a tacky substance containing a rubber as a major component and, on the other hand, provided, on its back side by coating, with a silicone-based release layer as described above (not shown). In such a rolled state, a release part in which the pressure-sensitive adhesive layer comprising a tacky substance containing a rubber as a major component contacts with the silicone-based release layer is constituted at the interfacial boundary between rolled layers.

FIG. 5 and FIG. 6 are examples in which a rolled tape T is used as a medical tape or a tape for packaging corrugated boards. Illustratively stated, by winding the tape T while lapping as in FIG. 5, a release part structure of the present invention is likewise constituted in the lap parts, and by coating the above-described silicone-based release agent beforehand on the seal part of the corrugated boards and sealing the seal part by applying the tape T (release treatment of its back side may be omitted) as in FIG. 6, a release part structure of the present invention is likewise obtained.

Figure 1:
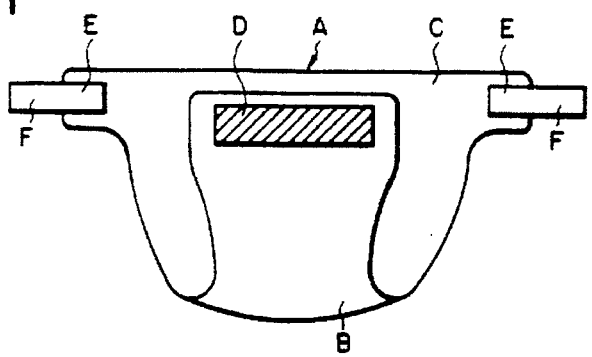
FIG. 1 is an illustrative view showing the construction of a paper diaper.
Figure 2:
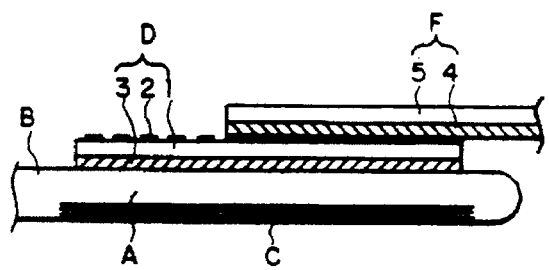
FIG. 2 is a sectional illustrative view showing an example of the present invention in a fastener part of a paper diaper.
Figure 3:
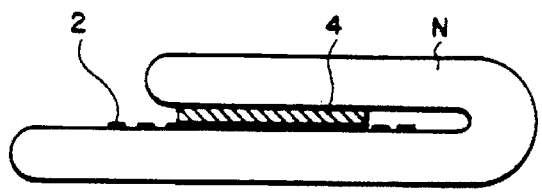
FIG. 3 is an illustrative view showing another application example of the present invention.
Figure 4:
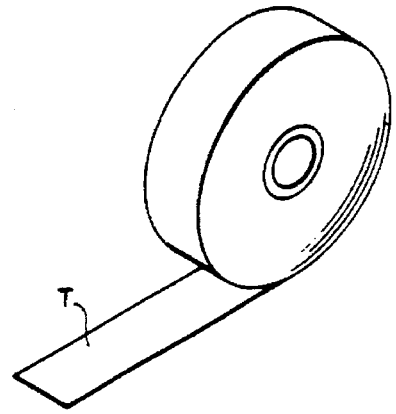
FIG. 4 is an illustrative view showing another application example of the present invention.
Figure 5:
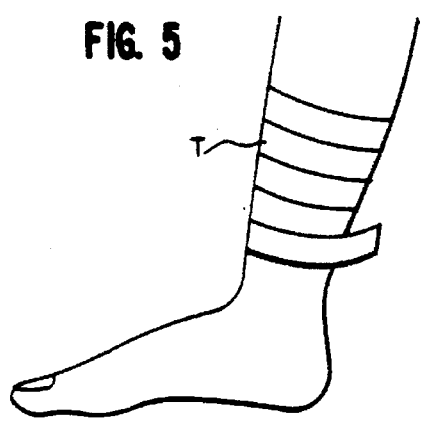
FIG. 5 is an illustrative view showing another application example of the present invention.
Figure 6:
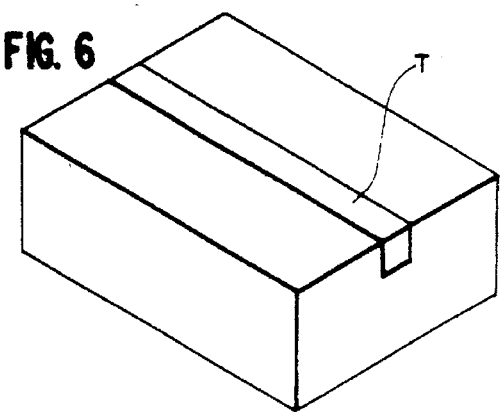
FIG. 6 is an illustrative view showing another application example of the present invention.
Description of the Symbols
1—Film
2—Silicone-based release layer
3—Adhesive
4—Pressure-sensitive adhesive layer
5—Tape support Best Modes for Carrying Out the Invention The present invention will be explained below in detail by means of examples. The "parts" appearing in the sentences mean parts by weight.

A toluene/xylene solution (solid content 30% by weight) of a three-dimensional structure organopolysiloxane (X-92-140 manufactured by Shin-Etsu Chemical Co., Ltd.) was mixed with a toluene solution (solid content 30% by weight) of an addition reaction type silicone (X-62-2378 manufactured by Shin-Etsu Chemical Co., Ltd.) having a viscosity of 1,500 cps at 25° C. in a manner such that the resulting solutions contained the three-dimensional structure organopolysiloxane at 10% by weight, 30% by weight, and 50% by weight, respectively.

Further, to these solutions a 1,000 ppm platinum complex with vinylsiloxane (PL-50T manufactured by Shin-Etsu Chemical Co., Ltd.) was added as a catalyst in an amount of 2 parts per 100 parts by weight of the above-described silicone composition.

Subsequently, this solution was coated as a release agent on a 12 µ-thick polyester film at 0.3 g/m² and then heat-treated at 120° C. for 1 minute to form a release layer, thereby obtaining release layer-side sample pieces 1, 2, and 3.

On the other hand, a low-density polyethylene film having a thickness of 120 µm was coated on one side at a thickness of 50 µm with a tacky substance containing a rubber as a major component and obtained by blending 40 parts of a styrene-isoprene-styrene copolymer with 40 parts of a petroleum resin as tackifier resin, 19 parts of a paraffin oil as softener, and 1 part of an anti-aging agent, whereby a pressure-sensitive adhesive layer was formed. This was cut into 70 mm-length×25 mm-width to give an adhesive tape-side sample piece.

This adhesive tape-side sample piece was applied to release layer-side sample pieces 1, 2, and 3 as Examples 1, 2, and 3 of the present invention. Each of these was subjected to bond strength tests (peel strength, shear bond strength, and holding power), and further subjected to a monitor test with the samples being actually applied to paper diapers.

Incidentally, the three-dimensional-structure organopolysiloxane content in Example 1 was 10% by weight, that in Example 2 was 30% by weight, and that in Example 3 was 50% by weight.

Comparative Examples

In Comparative Example 1, a three-dimensional-structure organopolysiloxane was not incorporated in the silicone-based release agent. In Comparative Example 2, in place of the silicone-based release agent, a 2% toluene solution of a long-chain alkyl type release agent (Peeloyl 1010 manufactured by Ipposha Oil Co., Ltd.) was coated at 0.5 g/m² and heat-treated at 80° C. for 30 seconds to give a release layer-side sample piece.

In Comparative Examples 3, 4, and 5, an acrylic pressure-sensitive adhesive (a copolymer of 2 ethylhexyl acrylate and acrylic acid: weight ratio 100/2) was coated for adhesive tape-side samples, in place of the tacky substance containing a rubber as a major component in Examples 1, 2, and 3.

The results of these are shown in Table 1.

Incidentally, each test method is as described later.

TABLE 1

| | Bond Strength Test | | | Monitor Test | | |
|---|---|---|---|---|---|---|
| | Peel strength (g/25 mm) | Shear bond strength (g/25 mm) | Holding power (min) | Easiness of peeling | Unsusceptibility to separation | Unloudness of peeling noise |
| Example | | | | | | |
| 1 | 40 | 1900 | 2 | o | o | o |
| 2 | 100 | 2700 | 7 | o | o | o |
| 3 | 140 | 3000 | 10 or more | o | o | o |
| Comparative Example | | | | | | |
| 1 | 5 | 100 | 0.01 | o | x | o |
| 2 | 350 | 3000 or more | 10 or more | o | o | x |
| 3 | 27 | 20 | 0.01 | o | x | o |
| 4 | 92 | 85 | 0.01 | o | x | o |
| 5 | 129 | 182 | 0.1 | o | x | o |

<Peel Strength>

The adhesive tape-side sample piece was applied, by means of one forward-and-backward movement of a 2 kg roller, to the surface of the release layer of each of release layer-side sample pieces 1, 2, and 3 which had been fixed to a stainless-steel plate, and within 3 minutes of the application, the 180° peel bond strength was measured at 300 mm/min.

<Shear Bond Strength>

One side part (25 mm×25 mm) of the adhesive tape-side sample piece was applied, by means of one forward-andbackward movement of a 2 kg roller, to the surface of the release layer of each of release layer-side sample pieces 1, 2, and 3 which had been bonded to a small piece cut out of a commercially available paper diaper, and the shear bond strength was measured by pulling away the other end part in the shear direction (pulling speed, 300 mm/min) by means of a Tensilon-type universal testing machine.

<Holding Power>

The samples prepared in the above-described shear bond strength test were held in the vertical direction and hung at a load of 1 kg, and the time period (min) to falling of the adhesive tape-side sample piece was measured.

<Monitor Test>

Each of the above-described sample pieces was actually applied to the fastener parts of paper diapers, and a monitor test was conducted by 10 people with regard to easiness of peeling, unsusceptibility to separation, and unloudness of peeling noise. Those regarded as good by 8 or more of the 10 persons were evaluated as o, those regarded as good by 5–7 persons as Δ, and those regarded as good by 4 or fewer persons as x.

Possibility of Industrial Application

As described above, the release part structure of the present invention has a feature that the tape or like part is difficult to separate when it should be kept fixed, and on the other hand, when it should be peeled away, noise-free peeling thereof is easy. Therefore, the structure is useful for forming the release parts of paper diapers and the like, as the structure of those release parts of other disposable absorbent articles which have been designed for peeling and fixing, and also as the structure of the release parts of medical tapes, packaging tapes, and the like.

In particular, the structure of the present invention which, when used for fastening paper diapers, is noise-free or enables noiseless peeling and meets the consumer demands is of great practical value in these days of increased spread of paper diapers with the consumed amount thereof per day being large and the frequency of use thereof being high at midnight.

What is claimed is:

1. A paper diaper release part structure having an interfacial boundary, wherein the release part structure comprises
(a) a silicone-based release layer coated on a reinforcing film on a back sheet of a paper diaper front part, and
(b) a fastener tape prepared by forming a pressure-sensitive adhesive layer on a tape support, wherein the fastener tape is attached to a paper diaper part other than the paper diaper front part,
wherein the interfacial boundary is constituted by the pressure-sensitive adhesive layer and the silicone-based release layer, and
wherein said adhesive layer comprises a tacky substance containing a rubber as a major component and said release layer comprises a silicone-based release agent containing a three-dimensional structure organopolysiloxane in an amount of 1–80% by weight, said three-dimensional structure organopolysiloxane having an average composition formula represented by $$(R_3SiO_{0.5})_a(R_2SiO)_b(RSiO_{1.5})_c(SiO_2)_d$$

wherein R is a monovalent hydrocarbon group, and a, b, c and d, which represent molar fractions of the respective siloxane units, are such that a is 0.1 to 0.6, b is 0 to 0.45, c is 0 to 0.3, and d is 0.3 to 0.8, provided that a/d is 0.3 to 2.0.

2. A paper diaper release part structure as claimed in claim 1, wherein the rubber component in the tacky substance is one mainly comprising an ABA-type or AB-type block copolymer, wherein A is a thermoplastic block and B is a rubber block.

3. A diaper having component parts which have formed thereon a silicone-based release layer and a pressure-sensitive adhesive layer of a release part structure having an interfacial boundary, wherein the release part structure comprises
(a) said silicone-based release layer coated on a reinforcing film on a back sheet of a paper diaper front part, and
(b) a fastener tape prepared by forming said pressure-sensitive adhesive layer on a tape support, wherein the fastener tape is attached to a paper diaper part other than the paper diaper front part,
wherein the interfacial boundary is constituted by the pressure-sensitive adhesive layer and the silicone-based release layer, and
wherein said adhesive layer comprises a tacky substance containing a rubber as a major component and said release layer comprises a silicone-based release agent containing a three-dimensional structure organopolysiloxane in an amount of 1–80% by weight, said three-dimensional structure organopolysiloxane having an average composition formula represented by $$(R_3SiO_{0.5})_a(R_2SiO)_b(RSiO_{1.5})_c(SiO_2)_d$$

wherein R is a monovalent hydrocarbon group, and a, b, c and d, which represent molar fractions of the respective siloxane units, are such that a is 0.1 to 0.6, b is 0 to 0.45, c is 0 to 0.3, and d is 0.3 to 0.8, provided that a/d is 0.3 to 2.0.

4. A diaper as claimed in claim 3, wherein the rubber component in the tacky substance is one mainly comprising an ABA-type or AB-type block copolymer, wherein A is a thermoplastic block and B is a rubber block.

* * * * *